United States Patent [19]

Rogers et al.

[11] Patent Number: 4,675,464

[45] Date of Patent: Jun. 23, 1987

[54] CHEMICAL DESTRUCTION OF HALOGENATED ALIPHATIC HYDROCARBONS

[75] Inventors: Charles J. Rogers; Alfred Kornel, both of Cincinnati, Ohio

[73] Assignee: Government of the United States as represented by the Administrator of the Environmental Protection Agency, Washington, D.C.

[21] Appl. No.: 883,785

[22] Filed: Jul. 9, 1986

[51] Int. Cl.⁴ ............................................. C07C 2/02
[52] U.S. Cl. ................................. 585/538; 585/612; 585/641
[58] Field of Search ..................... 585/538, 612, 641

[56] References Cited

U.S. PATENT DOCUMENTS

| | | | |
|---|---|---|---|
| 2,322,258 | 6/1943 | Strosacker et al. | 260/654 |
| 3,829,522 | 8/1974 | Schneider | 585/538 |
| 4,327,027 | 4/1982 | Howard et al. | 260/340.3 |
| 4,337,368 | 6/1982 | Pytlewski et al. | 568/730 |
| 4,353,793 | 10/1982 | Brunelle | 208/262 |
| 4,400,552 | 8/1983 | Pytlewski et al. | 568/715 |
| 4,447,541 | 5/1984 | Peterson | 435/264 |
| 4,579,992 | 4/1986 | Kaufhold et al. | 585/612 |

Primary Examiner—Curtis R. Davis

[57] ABSTRACT

Method for the total dehydrohalogenation of halogenated compounds. The method includes providing a reaction mixture by dissolving an alkali metal hydroxide in a molar excess of an ethylene glycol to form an alkali metal glycolate and reacting the halogenated organic compound with the alkali metal glycolate. In halogenated compounds having one carbon, carbon dioxide is the reaction product. In those having more than one carbon, acetylene is formed. The preferred ethylene glycol is tetraethylene glycol and the preferred alkali metal is potassium hydroxide. The method is particularly useful for disposing of toxic halogenated compounds which make up soil contaminants, like ethylene dibromide.

12 Claims, No Drawings

CHEMICAL DESTRUCTION OF HALOGENATED ALIPHATIC HYDROCARBONS

BACKGROUND OF THE INVENTION

The present invention is directed to a method for dehydrohalogenating halogenated compounds, and more particularly, to a safe and effective method for disposing of dangerous halogenated compounds like ethylene dibromide by dehydrohalogenation.

Ethylene Dibromide, also known as dibromo ethane (EDB), was at one time commonly used as a pesticide and spot fumigant. It has recently been determined that the use of EDB as a pesticide and spot fumigant is a major health risk to the general public and especially to people, like mill workers, who handle the products sprayed with EDB. The pesticide is now known to be carcinogenic to humans. Since EDB was also used as a fumigant at grain mills and at grain storage facilities, there is also a significant cancer risk to the general public via intake of those grains.

The toxic properties of EDB mandated the cancellation of its registration by the Environmental Protection Agency (EPA). This cancellation resulted in the need to dispose of thousands of gallons of EDB. Incineration is not considered a safe method. Accordingly, there is now a need for a safe and effective method to dispose of the cancelled EDB and similar compounds.

Known methods for destroying various halogenated compounds similar to EDB involve the use of polyethylene glycols. With several such methods, there does not appear to be any dehydrogenation. U.S. Pat. No. 4,327,027 to Howard et al describes the dehalogenation of 2,3,7,8-tetrachlorodibenzo-p-dioxin (TCDD) by reaction with an admixture of an alkali metal hydroxide and an alcohol. This process is completed at very high temperatures, generally at 160°-180° C. Pytlewski et al, U.S. Pat. No. 4,337,368 discloses the decomposition of polychlorinated biphenyl (PCB) by reaction with sodium polyethylene glycol and oxygen. The decomposition products are identified as polyhydroxylated aromatics.

A further method, in U.S. Pat. No. 4,353,793 to Brunelle, involves the dechlorination of PCB by reaction with low molecular weight polyethylene glycol ethers and potassium hydroxide. The reagant is described as a monocapped-polyalkyleneglycol alkyl ether.

U.S. Pat. No. 4,447,541 to Peterson dehalogenates various polyhalogenated compounds present in the soil as contaminants with a reagant comprising potassium hydroxide and polyethylene glycol. This reaction, however, requires a sulfoxide catalyst.

More relevant here is the Strosacker reference, U.S. Pat. No. 2,322,258, which discloses the dehydrohalogenation of polyhalo aliphatic hydrocarbons such as ethylene dibromide (EDB) to produce the corresponding halogenated olefin, in the case of EDB, vinyl bromide. The reagant is an admixture of a polyhydric alcohol, which is prefererably tetraethylene glycol, and an alkaline reactant, which may be potassium hydroxide. This process, however, uses approximately 0.0001 mole of the glycol catalyst per mole of the alkali metal and, consequently, the reactants must be heated to 50°-150° C. or in order for the catalyst to form a solution which will dissolve the alkali. A salt crust would otherwise form around the alkali and impede the reaction.

None of the known methods have met the criteria required to provide a safe and efficient process to destroy the halogenated compounds that comprise contaminants. Destruction of the compound without release of toxic pollutants into the environment is clearly important. Thus, a process which produces by-products that are not toxic is most important. It would be advantageous if the method could be conducted on-site and would not require specialized containers and equipment for handling the by-products. It is also desirable to have a process which does not require high temperatures.

Therefore, it is an object of the present invention to provide a method for the total dehydrohalogenation of halogenated compounds.

It is a further object of the present invention to provide a safe and efficient method to dispose of toxic soil and environmental contaminants containing one or more halogenated compounds by total dehydrohalogenation of the halogenated compound or compounds.

It is another object of the present invention to provide an on-site method to dispose of toxic environmental contaminants, like ethylene dibromide, which does not require high temperatures.

It is still another object of the present invention to provide a method for the total dehydrohalogenation of halogenated compounds which produces by-products that are non-toxic and do not require specialized containers and equipment for handling.

Still another object of the present invention is to provide a method for the dehydrohalogenation of halogenated compounds forming recoverable by-products which may be recycled or even sold.

SUMMARY OF THE INVENTION

The present invention is a method for the total dehydrohalogenation of at least one halogenated compound. The method includes providing a reaction mixture by dissolving an alkali metal hydroxide in a molar excess of an ethylene glycol to form an alkali metal glycolate, and reacting the halogenated organic compound with the alkali metal glycolate. In halogenated compounds having one carbon, carbon dioxide is the reaction product. In those having more than one carbon, acetylene is formed. The preferred ethylene glycol is tetraethylene glycol and the preferred alkali metal is potassium hydroxide. The reaction is self-initiating, self-sustaining and exothermic; therefore, additional amounts of the reactants may be added to continue the reaction. Preferably, the temperature of the reaction is kept at 30° C. or less to maintain the intermediate reaction products in solution until complete dehydrohalogenation occurs.

The method is particularly useful for disposing of toxic halogenated compounds which make up soil contaminants like ethylene dibromide, EDB.

DETAILED DESCRIPTION OF THE INVENTION

At the outset, the invention is described in its broadest overall aspect, with a more detailed description following. It should be pointed out that the method of the present invention is a method for the total dehydrohalogenation of a halogenated compound or a mixture of several halogenated compounds. This invention will have application in many areas and can be used in any situation where dehydrohalogenation of halogenated compounds is desired and on various halogenated compounds.

The present method is particularly useful for the destruction by dehydrohalogenation of ethylene dibromide (EDB) and compounds having similar chemical properties. The method is effective for halogenated compounds having one or more carbon atoms.

According to the method of the present invention, a reaction mixture is provided by dissolving an alkali metal hydroxide in a molar excess of an ethylene glycol to form an alkali metal glycolate. The alkali metal glycolate is reacted with the halogenated organic compound or the mixture containing several halogenated compounds.

Initially, a reaction mixture is formed in a reactor by dissolving an alkali metal hydroxide in a molar excess of an ethylene glycol. The reaction produces an alkali metal glycolate. In the reaction mixture, the molar ratio of the alkali metal hydroxide:ethylene glycol is preferably 0.5–1:1. The glycol serves to activate the alkali and convert it to a form which will be more reactive with the halogenated organic compound to be dehydrohalogenated.

The ethylene glycol used in the present invention may be diethylene glycol, triethylene glycol, tetraethylene glycol or pentaethylene glycol. The most effective potassium glycol bases for EDB dehydrohalogenation are the di-, tri-, and tetraethylene glycol ethers. Tetraethylene glycol is the preferred glycol because it is the most reactive in the process of the present invention. The reactivity of the lower molecular weight ethylene glycols is not as high as that of tetraethylene glycol and the reactivity of the glycols heavier than tetraethylene glycol decreases with their increasing molecular weight. These lower or higher molecular weight glycols form ethers which require heat to effect the otherwise incomplete dehalogenation. The most preferred ethylene glycol is tetraethylene glycol which does not require heating to activate the alkali metal hydroxide.

An alkali metal hydroxide is mixed with the glycol. It has been found that potassium hydroxide is the most reactive alkali in the context of this process. Potassium hydroxide may be introduced into the reaction as either the pellet or flake form to expedite initiation of the bromine elimination process. Further amounts of the alkali metal hydroxide may be added at a later time to allow the reaction to continue. Once the reaction is initiated, however, other alkali metal hydroxides will work as well to continue the reaction and a less expensive hydroxide, for example, sodium hydroxide, may be used.

Especially preferred is the use of an aqueous solution of potassium hydroxide to initiate the bromine elimination process. The preferred concentration of the aqueous solution is 30–70 wt. % of potassium hydroxide (KOH) in water. The most preferred concentration is about 40 wt. % KOH in water. In known methods for dehydrogenating halogenated compounds, water retarded the rate of the reaction. In the present invention, water increases the rate of the reaction. Furthermore, use of non-aqueous solvents may lead to the production of undesirable by-products. For example, the reaction of EDB with an alcoholic solution of KOH produces bromoethyl ether as a by-product.

The resulting alkali metal glycolate reacts with the halogenated organic compound to be dehydrohalogenated. If the halogenated organic compound has more than one carbon atom, as does EDB, acetylene is formed. If the compound has only one carbon atom, the method of the present invention produces carbon dioxide. Except for the differing resulting compounds, the method of the present invention is identical for one carbon halogenated compounds and for those having more than one carbon.

The ethylene glycol, alkali metal hydroxide and the halogenated compound may be added simultaneously to the reactor. In a preferred embodiment of this method, the alkali metal glycolate, formed from the reaction of the ethylene glycol with the alkali metal hydroxide, is prepared prior to the addition of the halogenated organic compound to the reaction mixture to increase the overall rate of the reaction.

The method of the present invention is further described with reference to one intended use of the method, that is, as a method for dehydrohalogenating EDB. This intended use, however, is merely illustrative and should not be considered as limiting.

The invention embodies a reaction between EDB and, in the preferred reaction sequence, potassium tetraethylene glycol (KTEG), under ambient conditions, 100% conversion of EDB to vinyl bromide, or, by two successive dehydrohalogenation reactions, to acetylene and potassium bromide. It appears that the reaction is a base catalyzed elimination reaction of the bromines from the EDB, since the proton transfer occurs simultaneously and the reaction can involve no intermediates as determined by gas chromotography/mass spectrometry analysis. The bromine eliminations for EDB dehydrohalogenation are:

$$BrCH_2CH_2Br + KTEG \rightarrow CH_2CHBr + KBr$$

$$CH_2CHBr + KTEG \rightarrow HC\ CH + KBR$$

The elimination of the bromines from EDB with KTEG is self-initiating, self-sustaining and exothermic.

The method is preferably conducted without heating. Moreover, in view of the exothermic nature of the reaction, cooling is preferable to control the temperature of the reaction mixture to 30° C. or less at all times. The lower temperature maintains the vinyl bromide, which has an extremely low boiling point and would otherwise be distilled off before it is further dehalogenated, in solution. Complete debromination of the brominated organic compound can occur, thereby ensuring that the final product is organohalogen free.

The reaction sequence of the present invention can be conducted at substantially atmospheric pressure. This feature is important to total EDB dehydrohalogenation; acetylene cannot safely be produced from the intermediate vinyl bromide under pressure because it will spontaneously detonate above 15 PSI. By conducting the reaction at atmospheric pressure, the danger or potential for detonation of the acetylene is avoided.

It should be noted that the method of the present invention is economical. The by-products, acetylene, carbon dioxide and potassium bromide, are non-toxic and do not require expensive specialized containers or equipment for their disposal. The by products are marketable and their value is expected to cover the entire cost of EDB disposal. Moreover, the ethylene glycols are not consumed in the reaction and can be recovered and used again.

In order to ensure that total dehydrohalogenation of EDB to form acetylene occurs, without the escape of vinyl bromide from the reacting solution, it is preferable that the reactor system include a reflux condensor chilled to a temperature below the boiling point of the vinyl bromide. Its purpose is to return the vinyl bromide to the reactor for a second debromination. The reflux condensor permits the large majority of the vinyl bromide to remain in the reaction system rather than distill off as a by-product.

Additional methods can be used to ensure than any residual vinyl halide still remaining in the gas stream is removed and returned to the reaction system. A scrubber may be used. A scrubber tower is packed with an inert inorganic material having a large surface area and filled with the KTEG-reagent solution. The large surface area ensures that the residual vinyl bromide will contact the surface and transfer from the gas phase. Alternatively, the gas stream could be vented through another reactor system to complete the dehalogenation.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for the dehydrohalogenation of at least one halogenated aliphatic hydrocarbon having two carbon atoms, said method comprising:

providing a reaction mixture by dissolving an alkali metal hydroxide in a molar excess of an ethylene glycol to form an alkali metal glycolate said ethylene glycol being selected from the group consisting of diethylene glycol, triethylene glycol, tetraethylene glycol and pentaethylene glycol; and reacting the halogenated organic compound with said alkali metal glycolate to produce acetylene.

2. The method of claim 1 wherein said ethylene glycol is tetraethylene glycol and said alkali metal is potassium hydroxide.

3. The method of claim 1 further comprising the step of:

adding additional amounts of said alkaline metal hydroxide, said ethylene glycol and said halogenated organic compound in approximately stoichiometric amounts to said reaction mixture.

4. The method of claim 3 wherein the alkaline metal hydroxide initially in the reaction mixture is potassium hydroxide and said alkali metal hydroxide added in additional amounts to the reaction mixture is sodium hydroxide.

5. The method of claim 1 wherein the temperature of said reaction mixture is kept at 30° C. or less.

6. The method of claim 1 further comprising the step of:

passing the gases emanating from the reacting step through a vent to a reflux condensor.

7. The method of claim 6 further comprising the step of:

passing the gases emanating from the reflux condensor through a scrubber containing additional amounts of the reaction mixture.

8. The method of claim 1 further comprising the step of:

passing the gases emanating from the reacting step through a vent to a scrubber containing additional amounts of the reaction mixture.

9. The method of claim 1 wherein all steps are conducted at substantially atmospheric pressure.

10. The method of claim 1 wherein the alkali metal hydroxide is used in the form of an aqueous solution.

11. The method of claim 1 wherein said alkali metal glycolate is prepared prior to addition of the halogenated organic compound to the reaction mixture.

12. The method of claim 2 wherein the molar ratio of potassium hydroxide:tetraethylene glycol in the reaction mixture is 0.5–1:1.

* * * * *